US007736311B2

(12) United States Patent
Bartnik et al.

(10) Patent No.: US 7,736,311 B2
(45) Date of Patent: Jun. 15, 2010

(54) SYSTEM FOR AUTOMATED MEASUREMENT OF SKIN PERFUSION PRESSURE

(75) Inventors: Daniel J. Bartnik, Eden Prairie, MN (US); Brandon W. Reynolds, Prior Lake, MN (US); Irvin T. Pierskalla, Prior Lake, MN (US)

(73) Assignee: Vasamed, Inc., Eden Prairie, MN (US)

( * ) Notice: Subject to any disclaimer, the term of this patent is extended or adjusted under 35 U.S.C. 154(b) by 747 days.

(21) Appl. No.: 11/468,203

(22) Filed: Aug. 29, 2006

(65) Prior Publication Data

US 2006/0287603 A1 Dec. 21, 2006

Related U.S. Application Data

(63) Continuation-in-part of application No. 11/197,971, filed on Aug. 5, 2005, now abandoned.

(60) Provisional application No. 60/609,175, filed on Sep. 10, 2004.

(51) Int. Cl.
*A61B 5/00* (2006.01)
(52) U.S. Cl. .................. 600/363; 600/504; 600/507
(58) Field of Classification Search ............... 600/504, 600/507, 323, 335, 334, 495, 496, 363, 322, 600/453–456, 300, 386, 391–392; 128/635, 128/668
See application file for complete search history.

(56) References Cited

U.S. PATENT DOCUMENTS 3,511,227 A    5/1970   Johnson

| 3,905,889 A | 9/1975 | Macur et al. |
| 4,016,863 A | 4/1977 | Brantigan |
| 4,109,647 A | 8/1978 | Stern et al. |
| 4,155,354 A * | 5/1979 | Rasmussen ................ 600/393 |
| 4,228,805 A | 10/1980 | Rosen et al. |

(Continued)

FOREIGN PATENT DOCUMENTS

WO    WO 94/23645    4/1994

(Continued)

OTHER PUBLICATIONS

Jin et al. (1997), "End-Tidal $PCO_2$ Serves as an Indicator of Cardiac Output During Experimental Septic Shock," *Crit. Care Med.* 25(1):A122 (Abstract).

(Continued)

*Primary Examiner*—Robert L Nasser
*Assistant Examiner*—Michael D'Angelo
(74) *Attorney, Agent, or Firm*—Barbara A. Wrigley; Oppenheimer Wolff & Donnelly, L.L.P.

(57) ABSTRACT

An automatic skin perfusion measuring system including instrumentation that automatically analyzes perfusion measurements to identify motion artifact and SPP values and a sensor placement device is provided. The instrumentation is configured to ignore motion artifact. Perfusion measurements are designated as SPP values if various criteria are met. SPP value criteria pertain to factors including cuff pressure, perfusion, perfusion change percentages relative to previous and subsequent perfusion measurements, and whether perfusion measurements are increasing or decreasing relative to previous and subsequent perfusion measurements. The sensor placement device assures reliable data is produced when multiple measurements are desired.

73 Claims, 11 Drawing Sheets

U.S. PATENT DOCUMENTS

| | | | |
|---|---|---|---|
| 4,230,122 A * | 10/1980 | Lubbers et al. ............. | 600/357 |
| 4,324,258 A | 4/1982 | Huebscher et al. | |
| 4,381,011 A | 4/1983 | Somers, III | |
| 4,503,859 A | 3/1985 | Petty | |
| 4,535,786 A | 8/1985 | Kater | |
| 4,538,618 A | 9/1985 | Rosenberg et al. | |
| 4,577,109 A | 3/1986 | Hirschfeld | |
| 4,590,948 A | 5/1986 | Nilsson | |
| 4,593,698 A * | 6/1986 | Athans ...................... | 600/386 |
| 4,596,254 A | 6/1986 | Adrian et al. | |
| 4,632,119 A | 12/1986 | Reichstein | |
| 4,643,192 A | 2/1987 | Fiddian-Green | |
| 4,729,384 A | 3/1988 | Bazenet | |
| 4,729,824 A | 3/1988 | Gilner | |
| 4,759,374 A | 7/1988 | Kierney et al. | |
| 4,785,814 A | 11/1988 | Kane | |
| 4,789,453 A | 12/1988 | Eberhard et al. | |
| 4,800,886 A | 1/1989 | Nestor | |
| 4,816,131 A | 3/1989 | Bomsztyk | |
| 4,833,091 A | 5/1989 | Leader | |
| 4,834,101 A | 5/1989 | Collison | |
| 4,842,783 A | 6/1989 | Blaylock | |
| 4,890,619 A | 1/1990 | Hatschek | |
| 4,892,383 A | 1/1990 | Klainer et al. | |
| 4,919,891 A | 4/1990 | Yafuso et al. | |
| 4,945,896 A | 8/1990 | Gade | |
| 4,966,148 A | 10/1990 | Millar | |
| 4,981,470 A | 1/1991 | Bombeck, IV | |
| 5,006,314 A | 4/1991 | Gourley et al. | |
| 5,098,659 A | 3/1992 | Yim et al. | |
| 5,105,812 A | 4/1992 | Corman | |
| 5,117,827 A | 6/1992 | Stuebe et al. | |
| 5,158,083 A | 10/1992 | Sacristan et al. | |
| 5,166,990 A | 11/1992 | Riccitelli et al. | |
| 5,174,290 A | 12/1992 | Fiddian-Green | |
| 5,251,619 A | 10/1993 | Lee | |
| 5,280,548 A | 1/1994 | Atwater et al. | |
| 5,297,556 A * | 3/1994 | Shankar ...................... | 600/481 |
| 5,329,922 A | 7/1994 | Atlee | |
| 5,330,718 A | 7/1994 | Hui et al. | |
| 5,341,803 A | 8/1994 | Goldberg | |
| 5,368,027 A | 11/1994 | Lubbers et al. | |
| 5,408,999 A | 4/1995 | Singh et al. | |
| 5,411,022 A | 5/1995 | McCue | |
| 5,423,320 A | 6/1995 | Salzman et al. | |
| 5,453,248 A | 9/1995 | Olstein | |
| 5,456,251 A | 10/1995 | Fiddian-Green | |
| 5,479,923 A | 1/1996 | Rantala | |
| 5,536,783 A | 7/1996 | Olstein et al. | |
| 5,579,763 A | 12/1996 | Weil et al. | |
| 5,596,988 A | 1/1997 | Markle et al. | |
| 5,607,644 A | 3/1997 | Olstein et al. | |
| 5,620,000 A | 4/1997 | Zinser et al. | |
| 5,631,340 A | 5/1997 | Olstein | |
| 5,672,515 A | 9/1997 | Furlong | |
| 5,714,121 A | 2/1998 | Alderete et al. | |
| 5,743,259 A | 4/1998 | Kruse | |
| 5,778,878 A | 7/1998 | Kellam | |
| 5,788,631 A | 8/1998 | Fiddian-Green | |
| 6,055,447 A | 4/2000 | Weil et al. | |
| 6,178,342 B1 * | 1/2001 | Borgos et al. ................ | 600/322 |
| 6,254,628 B1 * | 7/2001 | Wallace et al. ............. | 623/1.12 |
| 6,258,046 B1 | 7/2001 | Kimball et al. | |
| 6,501,973 B1 * | 12/2002 | Foley et al. .................. | 600/310 |
| 2003/0214408 A1 * | 11/2003 | Grajales et al. .......... | 340/573.1 |

FOREIGN PATENT DOCUMENTS

| | | |
|---|---|---|
| WO | WO 98/20794 | 5/1998 |
| WO | WO 00/59372 | 10/2000 |
| WO | WO 2005/030038 | 4/2005 |

OTHER PUBLICATIONS

Nakagawa et al. (1997), "Sublingual Capnometry for Quantification of the Severity of Hemorrhagic Shock," *Shock* 7:14 (Abstract).

Nakagawa et al. (1997), "ETCO$_2$ as Non-Invasive Indicator of Cardiac Output During Hemorrhagic Shock," *Crit. Care Med.* 25(1):A132 (Abstract).

Nakagawa et al. (1997) et al. (1997), "Sublingual Capnometry as an Indicator of Perfusion Failure in Human Patients," *Chest* 112:4S (Abstract).

Nakagawa et al. (1998), "Comparsion of Sublingual Capnometry with Gastric Capnometry and Lactate as Indicators of the Severity of Hemorrhagic Shock," *Crit. Care Med.* 26(1):A44 (Abstract).

Ogino et al. (1994), "Reflectance Pulse Oximeter Measuring Central Sa02 From Mouth," Proceedings of the Annual International Conference of the IEEE Engineering in Medicine and Biology Society, Baltimore, 2(16):914-915.

Peterson et al. (1984), "Fiber Optic Sensors for Biomedical Applications," *Science* 224(4645):123-127.

Sato et al. (1997), "Espohageal and Gastric PCO$_2$ Both Serve as Quantitative Indicators of Organ Blood Flow During Hemorrhagic Shock," *Crit. Care Med.* 25(19):A37 (Abstract).

Sato et al. (1997), "Esophageal PCO$_2$ as a Monitor of Perfusion Failure During Hemorrhagic Shock," *Appl. Physiol.* 82(2):558-562.

Seitz (1984), "Chemical Sensors Based on Fiber Optics," *Anal. Chem.* 56(1):16A-34A.

Tang et al. (1988), "Myocardial Preservation During Cardiopulmonary Resuscitation," *Curr. Opin. Crit. Care* 4:155-160.

Vurek et al. (1983), "A Fiber Optic PCO$_2$ Sensor," *Annals Biomed. Engineer* 11:499-510.

Weil (1998), "The Assault on the Swan-Ganz Catheter," *Chest* 113:1379-1386 (1998) (Invited Publication).

Xie et al. (1997) "Sublingual Capnometry for Quantitation of the Severity of Septic Shock," *Shock* 7:13-14 (Abstract).

Benazzo et al., "Endothelin-Induced Vasoconstriction in Rabbit Nasal Mucosa," *Acta Otolaryngol* (Stockh), vol. 114(5), pp. 544-546 (1994).

Bertuglia et al., "Venular Oscillatory Flow During Hemorrhagic Shock and No Inhibition in Hamster Cheek Pouch Microcirculation," *Microvascular Research*, vol. 54, pp. 23-242 (1997).

Casasco et al., "Occurrence, Distribution and Possible Role of the Regulatory Peptide Endothelin in the Nasal Mucosa," *Cell & Tissue Research*, vol. 274(2), pp. 241-247 (1993).

Friberg et al., "Habitual Snorers and Sleep Apnoics Have Abnormal Vascular Reactions of the Soft Palatal Mucosa on Afferent Nerve Stimulation," *The Laryngoscope*, vol. 108(3), pp. 431-436 (1998).

Grudemo et al., "Rhinostereometry and Laser Doppler Flowmetry in Human Nasal Mucosa: Changes in Congestion and Microcirculation During Intranasal Histamine Challenge," *ORL*, vol. 59, pp. 50-56 (1997).

Grudemo et al., "Studies of Spontaneous Fluctuations in Congestion and Nasal Mucosal Microcirculation and the Effects of Oxymetazoline Using Rhinostereometry and Micromanipulator Guided Laser Doppler Flowmetry," *American Journal of Rhinology*, vol. 13(1), pp. 1-6 (1999).

Hoke et al., "Blood-Flow Mapping of Oral Tissues by Laser Doppler Flowmetry," *International Journal of Oral & Maxillofacial Surgery*, vol. 23(5), pp. 312-315 (1994).

Jin et al., "Decreases in Organ Blood Flows Associated with Increase in Sublingual PCO$_2$ During Hemorrhagic Shock," *J. Applied Physiol.*, vol. 85(6), pp. 2360-2364 (1998).

Kelley et al., "Comparison Between the Uptake of Nitrous Oxide and Nitric Oxide in the Human Nose," *Journal of Applied Physiology*, vol. 85(4), pp. 1203-1209 (1998).

Klinger et al., "Untersuchungen zur Mikro-zirkulation der Nasenschleimhaut bei Verwendung von Ballon-tamponaden," ("The Influence of Cuffed Epistaxis Catheters on Nasal Mucosa Blood Flow Measured by Laser Doppler Flowmety") *Laryngo-Rhino-Otologie*, vol. 76, pp. 127-130 (1997).

Lacroix et al., "Sympathetic Vascular Control of the Pig Nasal Mucosa (III): Co-Release of Noradrenaline and Neuropeptide Y," *Acta Physiologica Scandinavica*, vol. 135(1), pp. 17-28 (1989).

Marais et al., "A Preliminary Comparison of the Effects of Halothane and Isoflurane on Nasal Mucosal Blood Flow," *Rhinology*, vol. 31(1), pp. 31-83 (1993).

Weaver et al., "Effect of Internal Maxillary Arterial Occlusion on Nasal Blood Flow in Swine," *The Laryngoscope*, vol. 109(1), pp. 8-14 (1999).

Ylipaavalniemi et al., "Éffect of Local Anaesthesia on the Blood Perfusion of Oral Mucosa Measured by the Laser Doppler Method," *Proceedings of the Finnish Dental Society*, vol. 79(2), pp. 58-61 (1983).

Vlad-Adrian Alexandrescu, M.D., et al., Selective Primary Angioplasty Following An Angiosome Model of Reperfusion in the Treatment of Wagner I-4 Diabetic Foot Lesions; Practice in a Multidisciplinary Diabetic Limb Service, J. Endovasc Ther, 2008, pp. 580-593, vol. 15, International Society of Endovascular Specialists, Belgium.

Richard F. Neville, et al., Revascularization of a Specific Angiosome For Limb Salvage: Does the Target Artery Matter?, Annals of Vascular Surgery, 2008, pp. 1-7, Elsevier, USA.

* cited by examiner

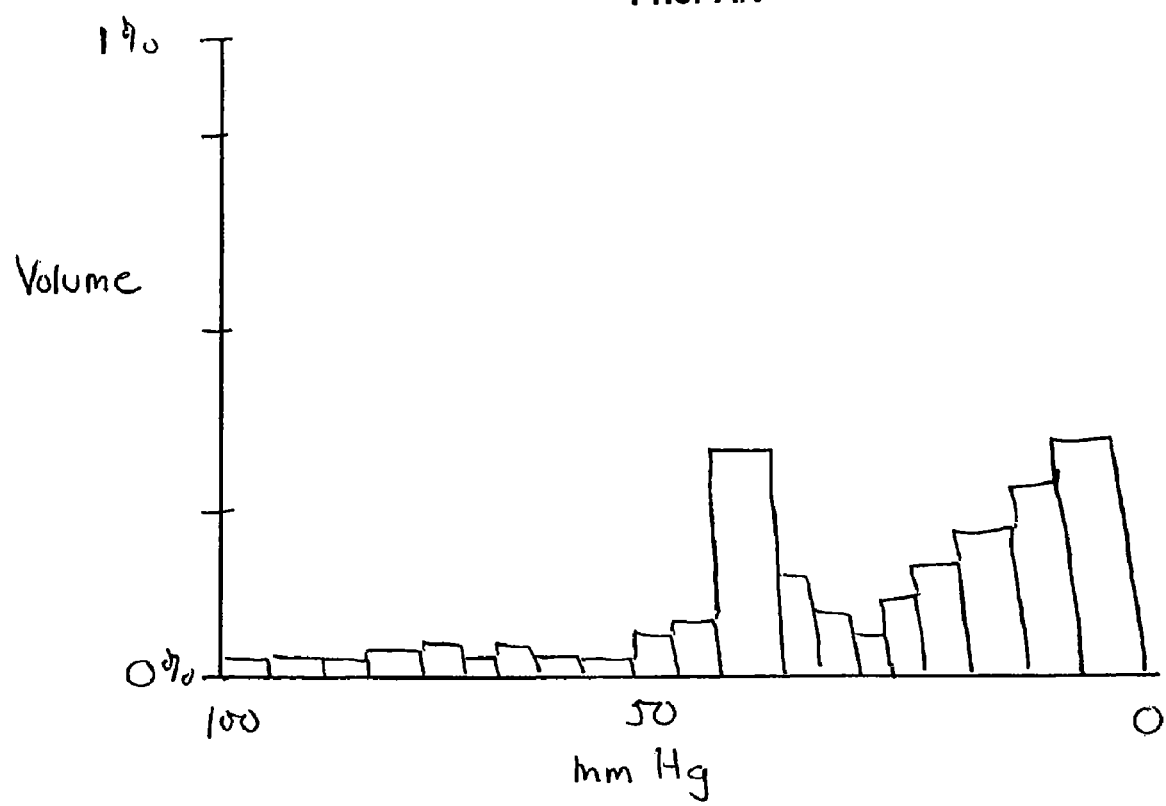

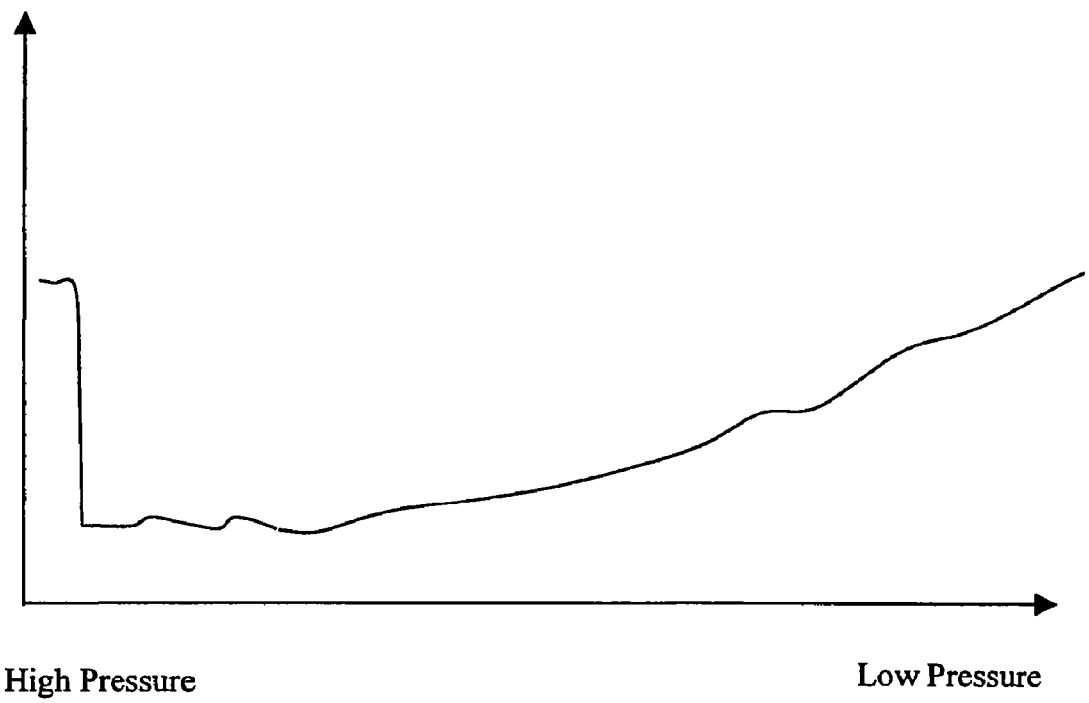

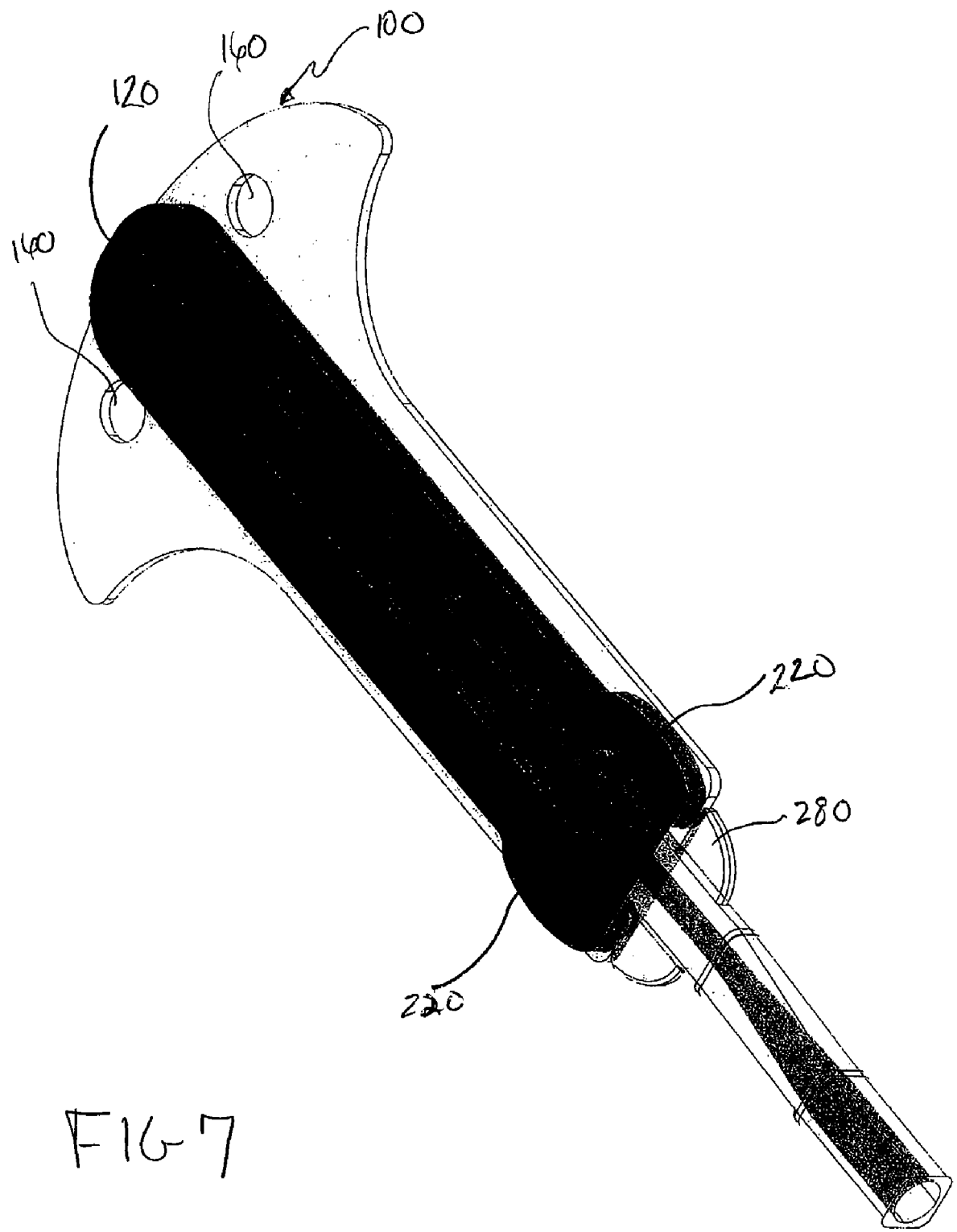

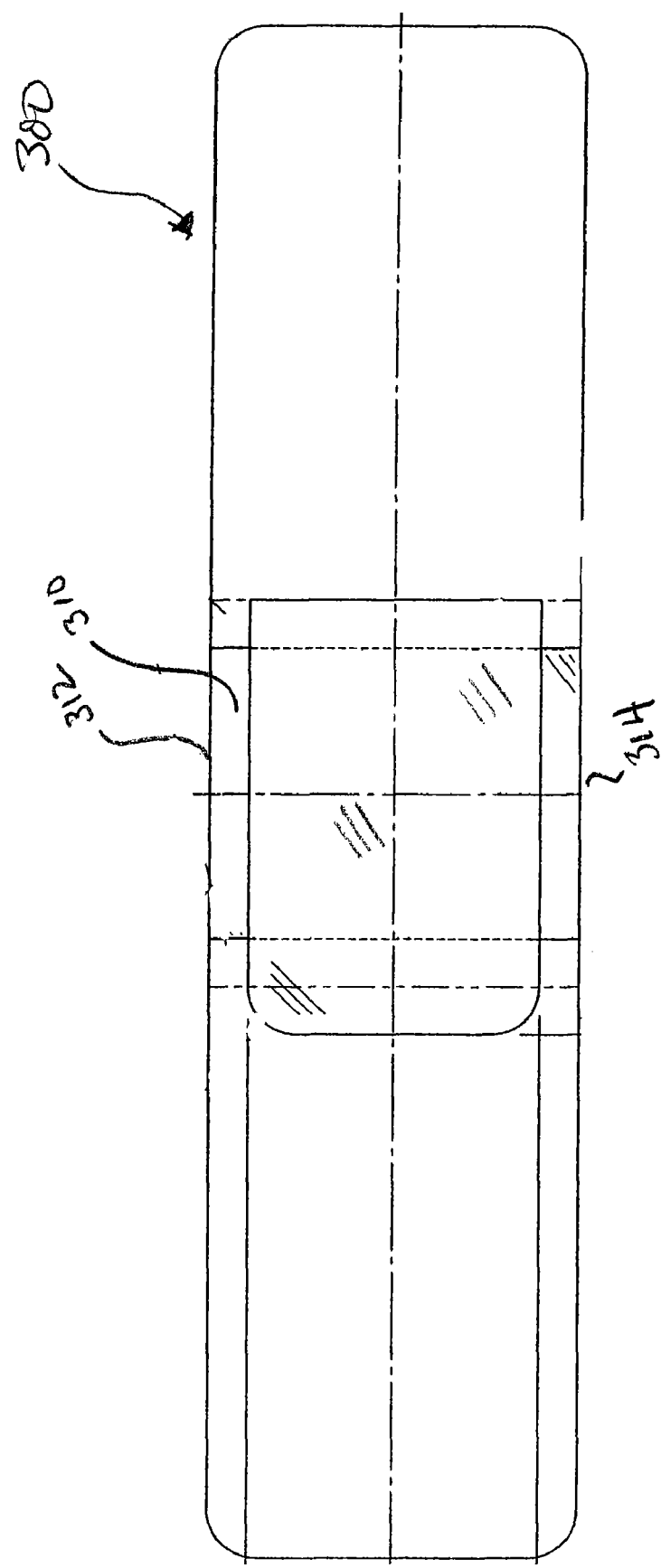

SYSTEM FOR AUTOMATED MEASUREMENT OF SKIN PERFUSION PRESSURE

CROSS REFERENCE TO RELATED APPLICATIONS

This application is a continuation-in-part of application Ser. No. 11/197,971, which claims the benefit under 35 USC 119(e) of U.S. Patent Application No. 60/609,175, filed Sep. 10, 2004, the entireties of which are hereby incorporated by reference.

BACKGROUND OF THE INVENTION

1. Field of the Invention

The present invention relates to a system for the automated measurement of skin perfusion pressure of a local or regional body site. More particularly the invention relates to a system that includes a measuring means for measuring capillary blood flow and placement means for assuring reproducibility, pressure means for applying pressure to a tissue site having capillary blood flow and means for measuring the applied pressure, and means for determining the relationship therebetween that detects and rejects motion artifact and indicates an SPP value.

2. Description of the Related Art

Skin perfusion pressure measurements are taken to determine whether local blood flow, i.e. capillary perfusion, of a local or regional body site having an ulcer or wound is sufficient to support wound healing. The accurate measurement of this parameter, therefore, is critical to physicians who treat patients suffering from open surface wounds resulting from complications from diabetes, pressure ulcers, burns, accidents, and the like.

Traditionally, skin or surface perfusion pressure is measured utilizing a surface or skin perfusion pressure-monitoring device coupled to a laser Doppler or other type of optical sensor. For example, U.S. Pat. No. 6,178,342 to Borgos et al. discloses a surface perfusion pressure instrumentation used in conjunction with a laser Doppler probe that measures the "amount" of moving blood contained within a microvascular observation volume in percent tissue hematocrit. This measurement is taken as a function of applied pressure. The laser Doppler optical probe defines an observation volume in the skin near the surface of the patient and a pressure cuff is used to manually apply pressure to the limb near the optical probe.

The laser Doppler sensor is placed against the skin under a pneumatic cuff that is secured to the affected limb, i.e. toe, ankle, arm, leg, etc. A user using an inflation bulb manually inflates the pneumatic cuff. The inflation pressure must be sufficiently high to stop local blood flow at the site of the optical probe. A display instrument is coupled to the optical probe typically via a fiber optic cable, and to the inflation bulb through a tube. Deflation starts and the optical probe monitors the number of moving red blood cells moving into or out of the observation volume without regard to velocity. The number of moving red blood cells detected within the control volume is expressed as a percent and displayed on the display monitor. This value is shown as both a numeric value and a bar graph on the Y-axis. The instrument also measures the pressure within the cuff and displays the applied cuff pressure in millimeters of mercury on the X-axis of the display. A moving bar chart along the X-axis shows the operator which cuff pressure is currently being measured. As pressure is slowly manually released, an indicator of blood flow return is provided in bar chart form. While a technician conducts the test, a physician interprets the data displayed on the display monitor.

Therefore, a significant problem with the use of skin perfusion pressure instruments described by Borgos et al. is that reliable, reproducible measurements are heavily dependent on operator/technician skill and the skill of the physician who interprets the surface perfusion pressure measurement. Another problem associated with manual deflation is that it is sensitive to motion artifact caused by the operator or patient (e.g. patient movement, pressure tubing movement, or sensor movement). In addition, motion artifact may result from patient movement, involuntary muscular movement, operator intervention, and other causes affecting the reading of skin perfusion pressure. If a patient moves the limb to which the sensor/pneumatic cuff is attached, the physician who makes the determination of the pressure at which flow returns might very easily err by reading "motion artifact" as the surface perfusion pressure measurement. When a skin perfusion pressure test is conducted on a sick patient, the physician is already expecting a low value for the surface perfusion pressure measurement. Consequently, given an occurrence of "motion artifact" the physician may interpret it as a skin perfusion pressure reading that is artificially higher than the actual skin perfusion pressure measurement.

For example, illustrated in FIG. 2A is a display from a prior art monitor. As can be seen, measured perfusion rises in percent value as the cuff pressure decreases. The physician conducting the skin perfusion test will likely record the value of skin perfusion pressure as forty-five millimeters of mercury. FIG. 2B again illustrates a display from a prior art monitor with the perfusion measurement rising in percent value as the cuff pressure decreases. However, motion artifact is now displayed at forty-five millimeters of mercury. A physician conducting the skin perfusion test may erroneously record the value of skin perfusion pressure as forty-five millimeters of mercury.

A further problem with conventional devices is that reproducibility is inhibited because when repeated measurements are needed the laser Doppler optical probe is not necessarily placed at the same site. Consequently, the surface perfusion pressure measurements may vary because the sensor is typically placed on a different site having different microcirculatory flow. For example, fiber optic probes may be placed directly on the surface of a patient's tissue underneath the pressure cuff. If repeated measurements are necessary, the fiber optic probe or sensor may not be placed on the same site in subsequent measurements.

In addition, if the fiber optic probe is used on several patients, this can create the risk of nosocomial infections, and other infections that originate in hospitals or healthcare settings. The problem with infection is sometimes dealt with by using disposable probes or sensors. However, disposable probes are more expensive than non-disposable or reusable probes and can also be time consuming to remove and replace. Routine removal and replacement of probes can also create equipment errors, calibration problems and overall system malfunctions and perhaps more importantly can affect reproducibility.

Another problem that exists with conventional systems is that the laser Doppler probe or sensor is sometimes placed underneath the pressure cuff or distal to the pressure cuff for measurement. Because the laser Doppler sensor is measuring the transmission of light, it would be ideal to provide for a device that is useful in eliminating ambient light from the measurement site.

Thus, there exists a need for a device that can be used in conjunction with probes that does not require disconnecting the probe from a monitoring system in order to replace it with a new probe and that can address the problem of reproducibility and ambient light.

Given the foregoing problems with conventional systems, there is a need for a system that (i) eliminates the need to disconnect a probe from surface perfusion pressure instrumentation to measure an alternate site or take a measurement on another patient; (ii) provides for a sensor placement device that can assure reproducibility where repeated measurements are required and reduces ambient light; and (iii) compensates for, or eliminates, motion-induced artifacts in patient-attached critical care monitoring instruments. In addition, there is a need for a system that increases reliability and reproducibility by eliminating user-created error for example, variable inflation and deflation and/or variable interpretation of the results. A new and improved skin perfusion system that includes a sensor placement device and that automatically inflates and deflates the pressure cuff, controls inflation and deflation, and detects and rejects motion artifact, and automatically determines an SPP value is needed.

BRIEF SUMMARY OF THE INVENTION

Accordingly it is an object of the present invention to overcome the problems and disadvantages of the surface perfusion pressure instruments of the prior art. It is, therefore, an object of the present invention to automate the measurement of skin perfusion pressure and generate an SPP value.

It is a further object of the present invention to provide a skin perfusion pressure system that automatically inflates and deflates and controls the inflation pressure and deflation rate of cuff pressure.

It is a further object of the invention to provide a skin perfusion pressure monitoring system that automatically detects and rejects motion artifact.

It is a further object of the invention to provide a skin perfusion pressure monitoring system that uses a perfusion sensitive tolerance that progressively adjusts sensitivity thresholds as perfusion returns.

It is a further object of the invention to provide a skin perfusion pressure monitoring system that actively controls the rate of cuff deflation.

It is a further object of the invention to provide a skin perfusion pressure monitoring system that determines when motion is severe enough to affect either the rate of cuff deflation or an accurate determination of an SPP value.

It is a further object of the invention to provide a skin perfusion pressure monitoring system that does not report an SPP value if motion is determined to be too severe or if the resulting SPP waveform does not have a recognizable perfusion signature.

It is a further object of the invention to provide a skin perfusion pressure monitoring system that evaluates duration of perfusion change.

It is a further object of the invention to provide a skin perfusion pressure monitoring system that evaluates the profile of perfusion change.

It is a further object of the invention to provide a reliable means to secure an SPP sensor to the tissue measurement site to improve reproducibility where multiple measurements are required, to reduce the risk of nosocomial infections, to reduce the need for disposable sensors, to reduce the likelihood that ambient light will affect the measurement outcome, and to insure that the connection between the automated system and the sensor is maintained.

In a first embodiment of the present invention the system includes capillary blood flow measuring means in communication with a tissue site having capillary blood flow therewithin; pressure means for simultaneously applying controllable pressure to said capillary blood flow measuring means and the tissue, the pressure means responsive to an automated sequence, the automated sequence comprising (i) occluding capillary blood flow within said tissue; and (ii) controllably releasing said pressure while capillary blood flow returns; measuring means for measuring the applied controllable pressure; and display means for displaying the relationship between said applied controllable pressure and said capillary blood flow, said display means in communication with said capillary blood flow measuring means and said applied controllable pressure means.

In a further embodiment of the present invention a sensor placement device for securing the capillary blood flow means to the tissue site is provided.

In another embodiment of the present invention a skin perfusion pressure monitoring system that automatically calculates the SPP value from perfusion measurements is disclosed. The monitoring system controls and measures cuff pressure and closely controls the rate of cuff deflation during the critical deflation portion of the skin perfusion pressure test cycle.

In another embodiment of the present invention, the monitoring system uses a perfusion sensitive tolerance that progressively adjusts sensitivity thresholds as perfusion returns. This allows for measurements of perfusion over a wide dynamic range while being less sensitive to motion transients.

In another embodiment of the present invention, the monitoring system actively controls the rate of cuff deflation and determines when motion is severe enough to affect this rate. The test is ended if motion is determined to be too severe.

In another embodiment of the present invention, the monitoring system monitors duration of perfusion change. As microcirculation returns it produces a perfusion signal that changes from baseline flow. Motion aritfact, on the other hand, produces a perfusion signal that has greater oscillatory content.

In another embodiment of the present invention, the monitoring system monitors the profile of perfusion change. As both macrocirculation and microcirculation normal flow resumes, it produces a change in perfusion signals that have recognizable and differentiable patterns. Motion artifact, on the other hand, produces a perfusion signal that is generally random, short-lived, and has more oscillatory content. Therefore, changes that do not follow a perfusion return signature are ignored by the monitoring system of the present invention. In addition, there are known perfusion return signatures that do not have a signature amenable to the automated qualification of an SPP value and the data can be displayed for the physician to interpret. For example, non-reactive hyperemia is a circulatory condition that results in such a known perfusion pattern.

These and other objects and advantages of the present invention will become apparent during the course of the following detailed description and appended claims. The invention may best be understood with reference to the accompanying drawings, wherein an illustrative embodiment is shown.

BRIEF DESCRIPTION OF THE DRAWINGS

FIG. 2B is a schematic diagram of a prior art display monitor illustrating motion artifact as a spiked bar;

FIG. 5D is a schematic diagram illustrating the pressure line output display in a circulatory condition known as non-reactive hyperemia.

FIG. 7 is a perspective view of a sensor placement device having an SPP sensor positioned therewithin in accordance with the present invention.

FIG. 8 is a top plan view of an alternative embodiment of a sensor placement device.

DETAILED DESCRIPTION OF THE INVENTION

Before the inventive devices and methods are disclosed and described, it is to be understood that certain terminology is used to describe the invention but different aspects of it may vary. It is also to be understood that the terminology used herein is for the purpose of describing particular embodiments only and is not intended to be limiting.

It must be noted that, as used in the specification and the appended claims, the singular forms "a," "an," and "the" include plural referents unless the context clearly dictates otherwise.

The term "adequate perfusion" means the perfusion criteria used to continue the cuff inflation sequence. This criterion ensures that there is proper contact between the probe and the patient's skin. It is typically perfusion that is greater than 0.1%.

The term "no flow" means the perfusion criteria at which cuff deflation is initiated and is approximately less than 0.1%.

The term "baseline flow" means the flow between the determination of "no flow" and qualified SPP value.

The term "motion artifact" means the absence of the characteristic patterns of perfusion return including caregiver, operator or environmental influences such as patient movement, voluntary and involuntary muscle contraction, unwanted noise, and caregiver and operator interference.

The term "perfusion measurement" is the calculation proportional to the AC/DC ratio of the signals acquired by a perfusion sensor measured at an applied cuff pressure.

The term "perfusion percent" means the quantitative measure of capillary blood flow as relative to that of maximally perfused tissue.

The term "pressure cuff" or "cuff" and similar references means a pneumatic cuff or any device that applies pressure to the site, e.g. from above, adjacent the site, circumferentially, etc.

The term "$P_0$" is the perfusion measurement that is being evaluated or qualified for an SPP value.

The term "return flow" means the resumption of normal microcirculatory flow.

The term "skin perfusion pressure value" or "SPP value" represents the cuff pressure at which microcirculatory flow returns to the observation volume of tissue during the cuff deflation portion of the test.

Surface Perfusion Pressure System

Figure 1:
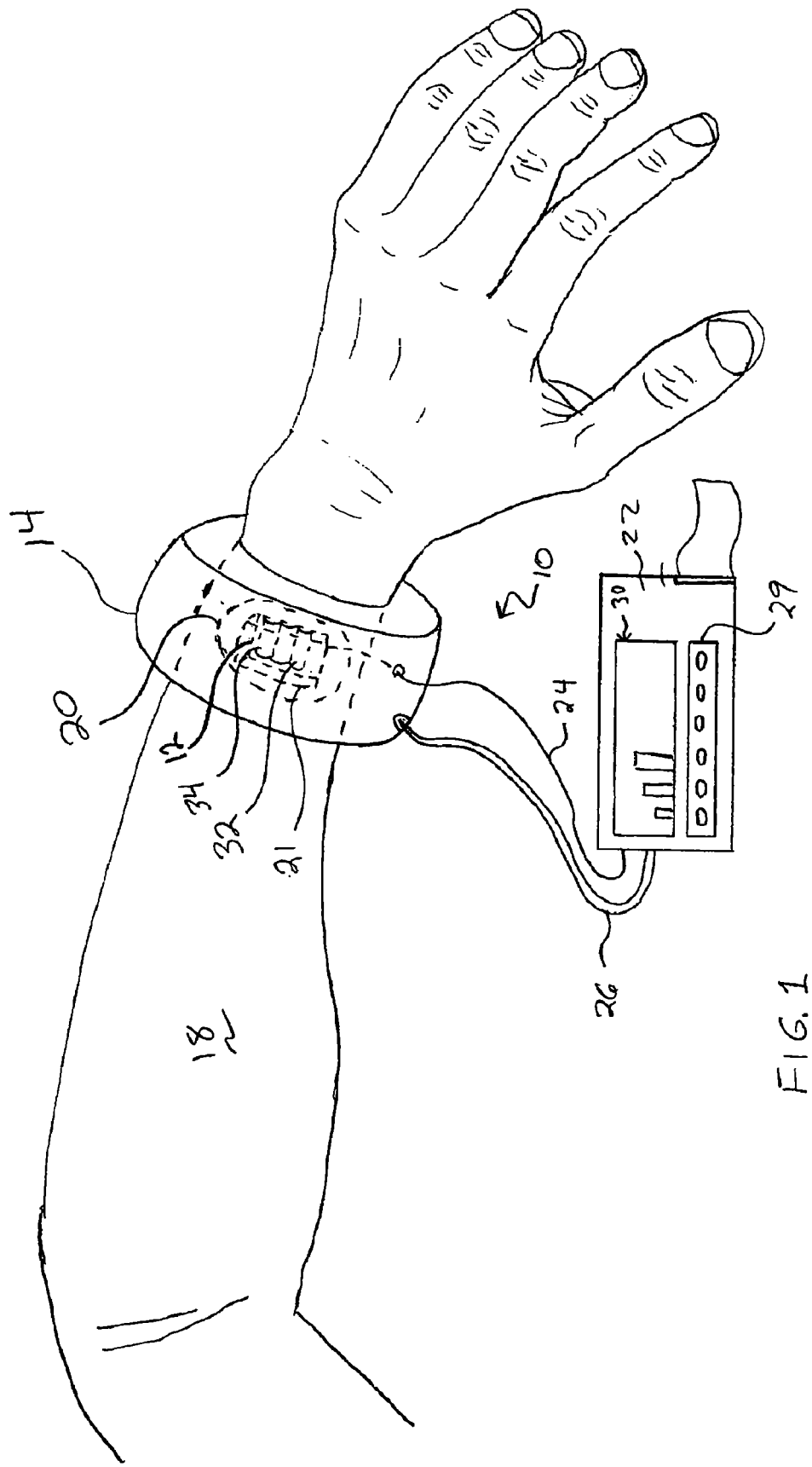
FIG. 1 is a schematic representation of the perfusion pressure monitor in use with a patient.
Figure 2A:
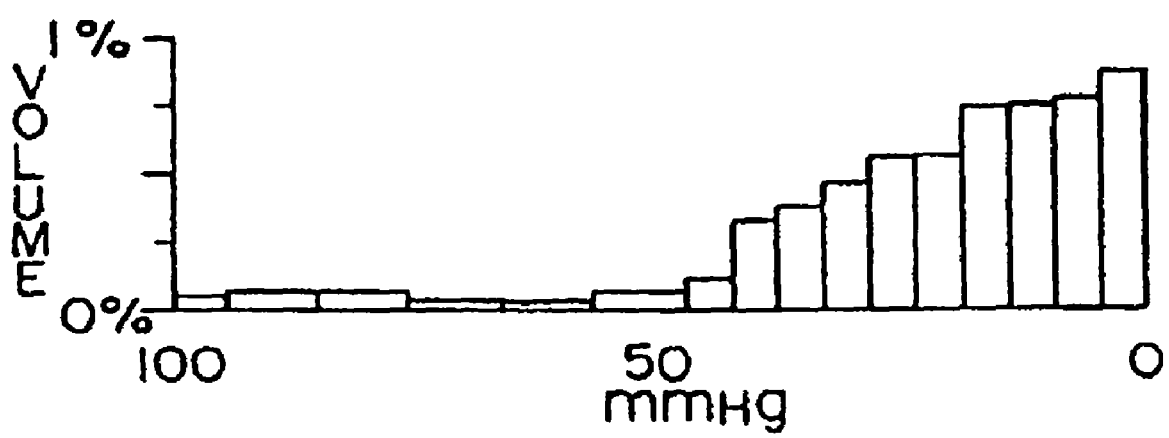
FIG. 2A is a schematic diagram of a prior art display monitor illustrating bars in a normal test progression.

Referring to FIG. 1, a schematic diagram depicting a representative, but not limiting, perfusion pressure monitoring system 10 is illustrated. The skin perfusion pressure monitoring system 10 broadly includes optical probe or sensor 12, pressure cuff 14, and skin perfusion pressure instrument 22 with display monitor 30. The optical probe 12 is positioned underneath pressure cuff 14 proximate the skin of the patient's limb 18. Alternatively, optical probe 12 may be positioned distal to cuff 14 or inside cuff bladder 14. In an alternative embodiment, cuff 14 may include a transparent window to observe optical probe 12. The skin perfusion pressure instrument inflates the pressure cuff 14 through tube 26. The size of pressure cuff 14 may be varied depending on whether the limb involved is the arm, toe, leg, ankle, etc. but must be capable of sustaining a sufficiently high pressure (above systolic) to stop local blood flow at the site of the optical probe 12 in the observation volume of tissue 20. The observation volume of tissue 20 may be at the same location as the applied pressure, at a location near the applied pressure, or distal from the applied pressure, e.g. where flow is measured on the toe and pressure is applied at the ankle. The skin perfusion instrument 22 is coupled to the optical probe 12 via a fiber optic cable 24, and the pressure cuff 14.

Figure 5A:
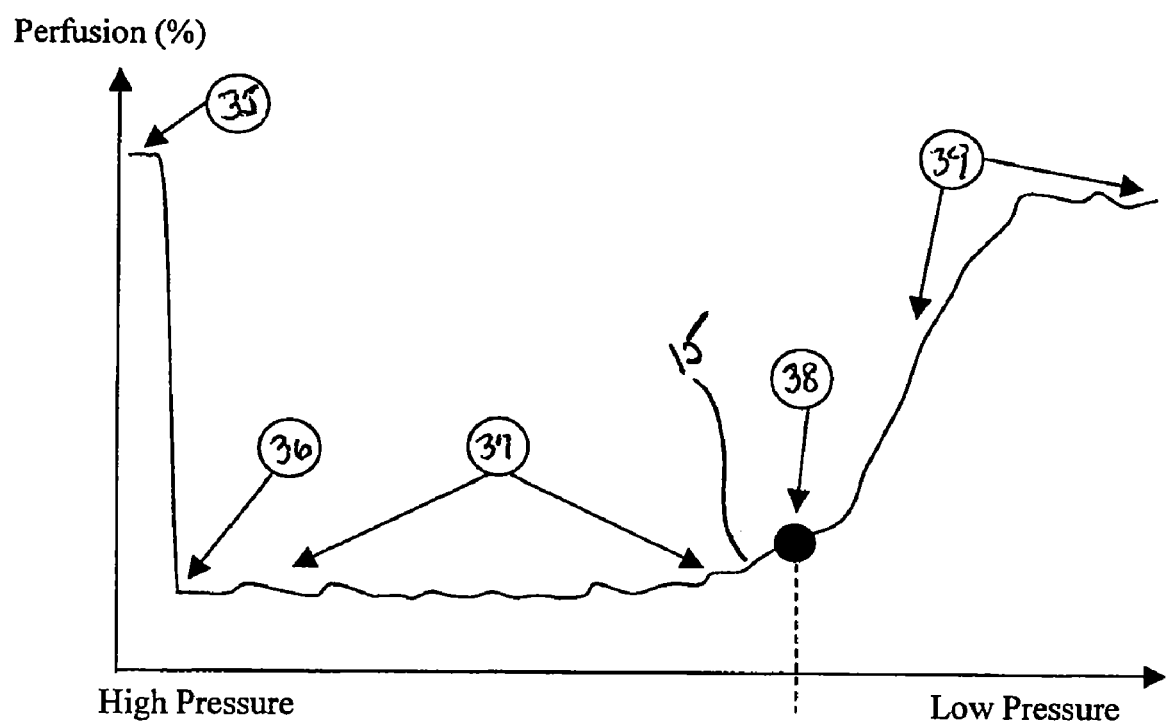
FIG. 5A is a schematic diagram illustrating the pressure line output display of the skin perfusion pressure monitoring system in accordance with the present invention.
Figure 5B:
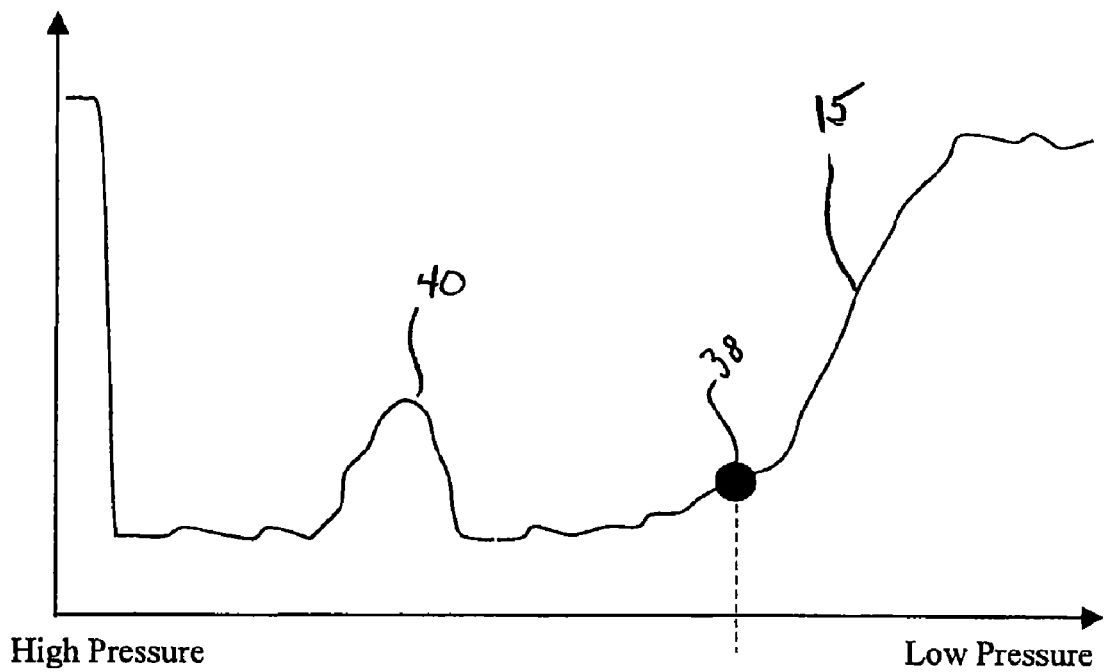
FIG. 5B is a schematic diagram illustrating the pressure line output display of the skin perfusion pressure monitoring system in accordance with the present invention with a spike indicating motion artifact.
Figure 5C:
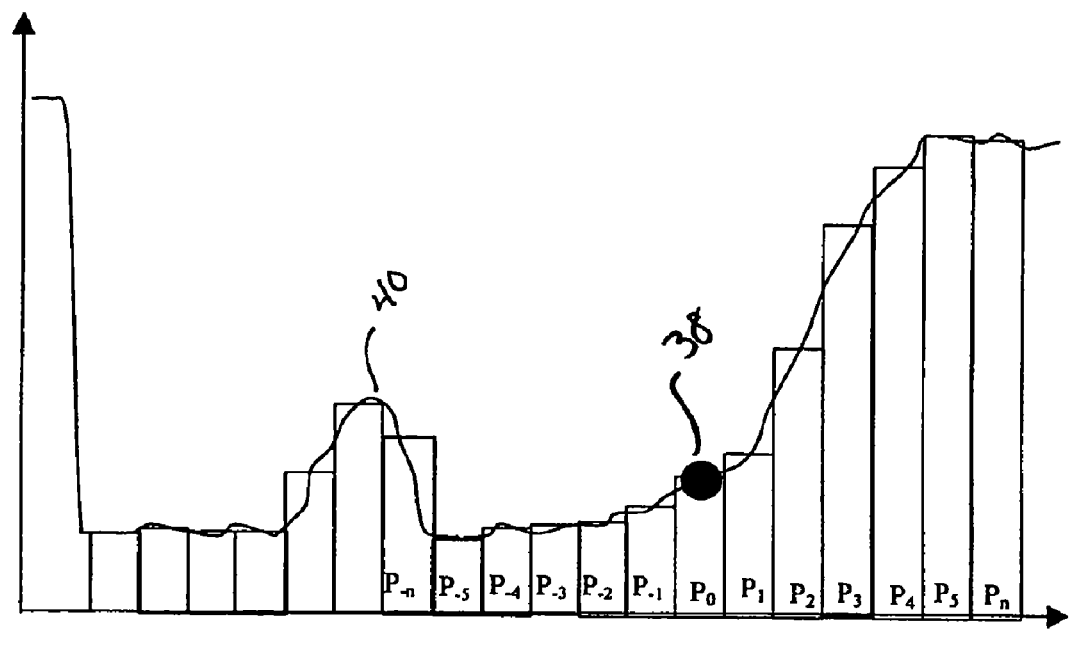
FIG. 5C is a schematic diagram illustrating the pressure line output display of the skin perfusion pressure monitoring system in accordance with the present invention with a spike indicating motion artifact, bars, and a true reading of surface perfusion pressure.

The optical probe 12 monitors microcirculatory flow within the observation volume of tissue 20. Microcirculation detected within the observation volume of tissue 20 is expressed as a percent and displayed on the Y-axis of the perfusion pressure display instrument. As best seen in FIG. 5C, the percent value is shown as both a numeric value, typically from 0% to 10% and graphically is shown as a bar graph on the Y-axis of the instrument display 30. The skin perfusion pressure instrument 22 also measures the pressure within the cuff 14 and displays the applied cuff pressure in millimeters of mercury on the X-axis of the display in descending uniform increments. As best seen in FIGS. 5A-B line 15 moves along the X-axis and shows the operator the cuff pressure that is currently being measured.

Optical probe 12 depicted in FIG. 1 includes at least a laser transmitter fiber 32 and at least one receiver photodiode 34. In an alternative embodiment, the laser or photodiode, or both, may be placed in probe 12 without a need for fiber optic elements. In operation, coherent light supplied from a solid state, or other laser device within the perfusion pressure display instrument 22 is conducted to the transmitter fiber 32 that is in contact with the patient's skin through the pressure cuff 14 bladder. Photons emitted from the transmit fiber 32 are scattered by the patient's tissues. A small portion (less than 5%) of the emitted photons is collected by the receiver fiber 34. The spacing between the fibers and the optical apertures of the fibers establish the volume of tissue that is monitored. Typically a single transmitter fiber is used with a pair of receiver fibers. The nominal fiber core diameter is on the order of 50 to 100 microns and is used to establish an observation volume of approximately one to two cubic millimeters. A suitable optical probe is disclosed in U.S. Pat. No. 5,654,539 to Borgos, the entirety of which is hereby incorporated by reference.

Notwithstanding, those skilled in the art will recognize that there are many ways to determine the point at which microcirculatory flow returns to a given observation volume. For example, visual observation such as the change in color of the observation site; ultra-sound; optical plethysmography, measurements of increases in temperature; sound, e.g. a microphone for pulsatile flow in the macrocirculation; metabolic indicators such as $pCO_2$ or lactate; and bioimpedance or pulse oximetry or both, each with a pulsatile measurement and a blood volume measurement.

Some back-scattered photons are frequency shifted by moving cells present in the microcirculation. The collected photons are collected by the skin perfusion pressure instrument 22 via cable 24 where they impinge on a photodiode. Thus, photons are impinging on the photodiode as a result of scattering off moving and stationary cells. The photodiode voltage contains both frequency and power information. The Doppler shifted frequency is related to cell velocity while the spectral power information is related to the volume of moving cells at that given frequency. The DC signal component results from the total number of photons received by the receive fiber 34. The AC signal component results from the mixing of frequency shifted photons with photons from stationary structures. If the number of moving cells present within the observation volume increases then the magnitude of the AC component will increase while the DC offset will remain nearly constant. The AC component increases because more returned photons undergo a Doppler shift. The DC component remains nearly constant because the total number of photons scattered by collisions with stationary cells within the measurement volume is reduced only slightly by moving cells. Therefore, the perfusion measurement is proportional to the ratio of the AC signal to the DC signal, which is an indication of the volume of moving cells in the observation volume of tissue. This type of measurement is commonly computed with both analog and digital signal processing. For example, it is common to convert the AC signal to an RMS equivalent through analog processing. It is these values that are presented to the A/D converter. The microprocessor then may square these digitized values prior to forming the ratio. The ratio value may be scaled by an empirically derived scaling factor that depends on the gain distribution throughout the signal processing paths.

Figure 3:
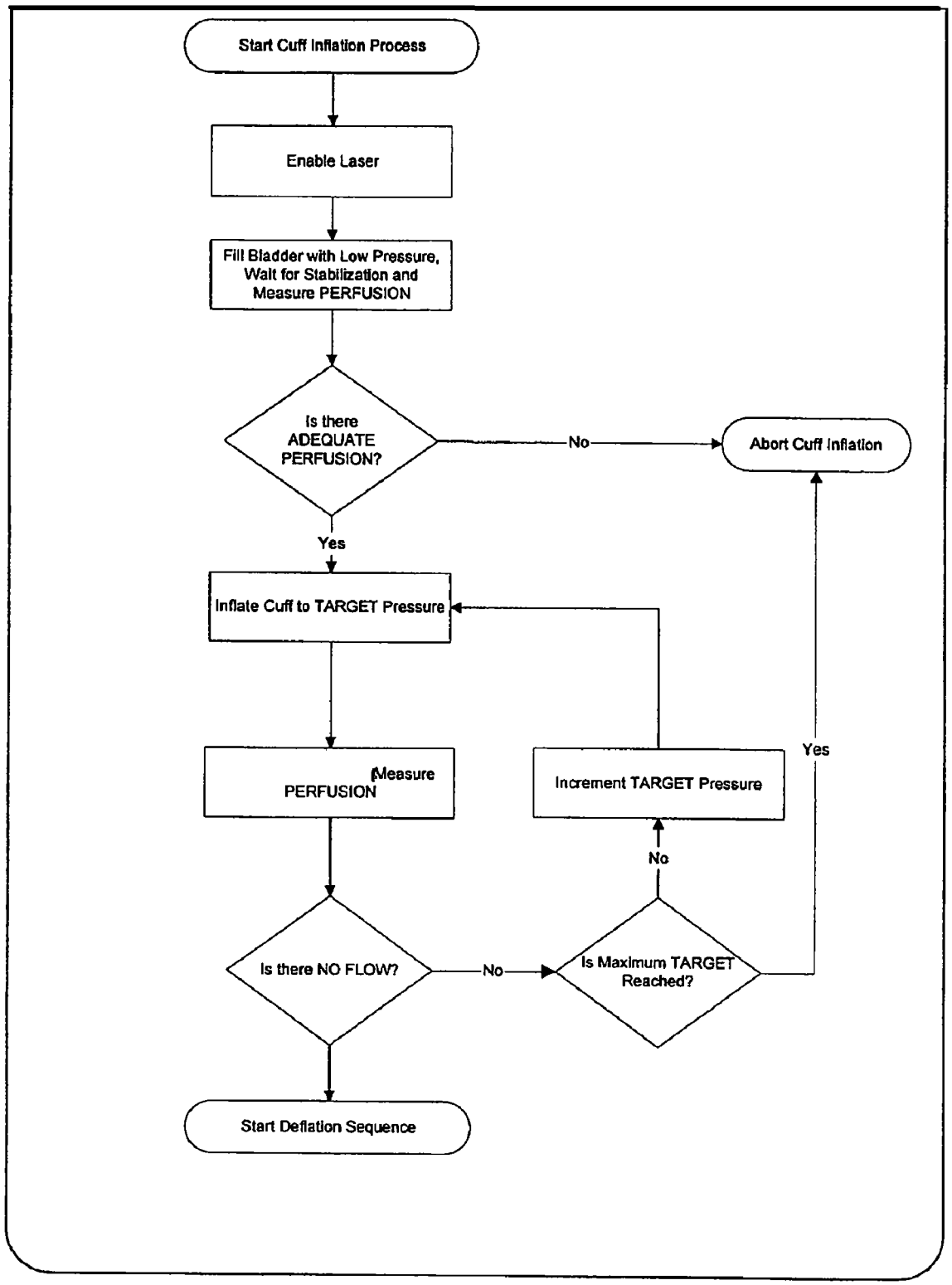
FIG. 3 is a flowchart representing the operation of the perfusion pressure monitor with respect to inflation.

Referring now to FIGS. 1 and 3, the cuff inflation sequence is illustrated. The skin perfusion instrument 22 commences the cuff inflation process and the laser in optical probe 12 is enabled. The cuff 14 bladder is initially filled with a low pressure, such as 5 to 10 mmHg, to ensure that the sensing probe is in contact with the patient's skin so that adequate perfusion can be detected and measured. If adequate perfusion cannot be measured, cuff inflation is aborted and the test does not proceed. If adequate perfusion can be measured, the pressure cuff 14 is inflated to the target pressure, near or at systolic and perfusion is measured. If "no flow" is not achieved at this target pressure and the maximum target pressure has not been reached, pressure is increased incrementally (e.g. 40 mmHg increments) and the "no flow" criteria is tested again. If the maximum target pressure has been reached, and the "no flow" criterion still has not been met, cuff inflation is aborted and the test discontinued.

Figure 4:
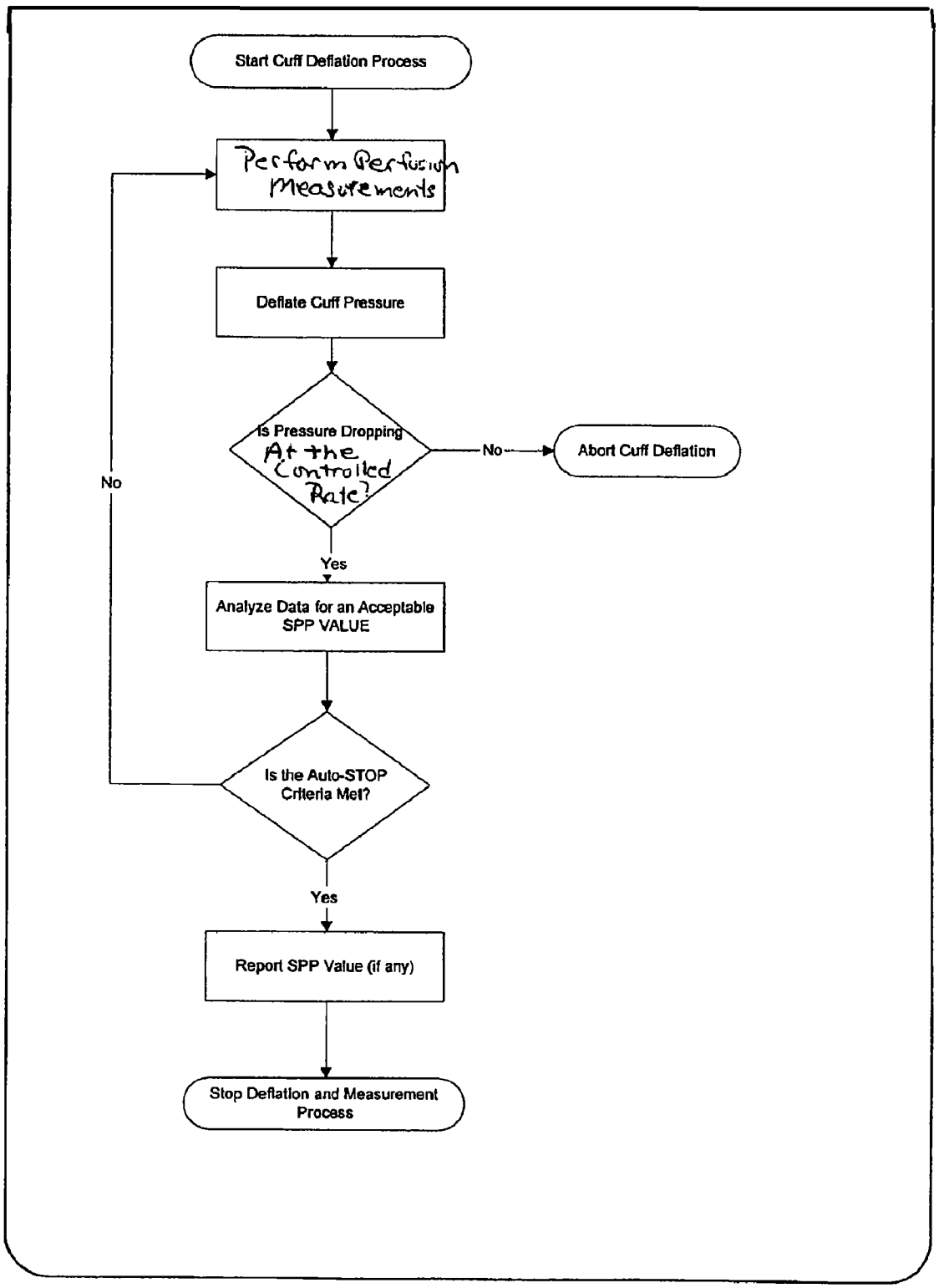
FIG. 4 is a flowchart representing the operation of the perfusion pressure monitor with respect to deflation.

FIG. 4 depicts the cuff deflation sequence. As noted above, if the skin perfusion pressure instrument recognizes a "no flow" signal, cuff pressure starts to automatically deflate at a controlled rate. A controlled rate of deflation provides reproducibility from measurement to measurement on the same patient and between patients. If the pressure is not dropping at the controlled rate, which may be caused by severe patient movement, cuff deflation is aborted and the test discontinued. If the pressure is dropping at the controlled rate, $P_0$ is analyzed for an SPP value. If all conditions for an SPP value are met, e.g. those discussed below, an SPP value is reported. If the conditions are not met, the test continues for a specified time period after which perfusion measurements are displayed for the physician to interpret but an SPP value is not reported for that test. The physician can then use the displayed perfusion data along with any other information that is available to her to determine whether another test should be conducted or if based on her expertise, she can determine an appropriate SPP value.

FIGS. 5A-D illustrate different stages of output data as depicted on the display monitor. Referring to FIG. 5A data being recorded during the testing procedure is displayed. Moving line 15 rises as pressure decreases. As can be seen, points representing adequate perfusion 35, no flow 36, baseline flow 37, SPP value 38, and the return of normal microcirculation 39 are depicted. FIG. 5B illustrates the same pressure line that rises as pressure decreases but now displays motion artifact 40. As illustrated, the skin perfusion pressure monitoring system in accordance with the present invention rejects motion artifact as not being a perfusion measurement and the test continues as seen by continuing line 15. Referring to FIG. 5C, the skin perfusion pressure monitor in accordance with the present invention analyzes numerous different criteria for detecting and rejecting motion artifact in qualifying $P_0$ for a SPP value. If $P_0$ has been qualified as an SPP value, a bar graph is overlaid on line 15, as best seen in FIG. 5C, and the SPP value 38 is recorded. As those skilled in the art can appreciate, any graphical representation can be used to depict the perfusion measurement data set. The skin perfusion pressure monitoring system 10 considers unique criteria in qualifying $P_0$ as an SPP value and in assessing whether motion artifact is present. Those skilled in the art can appreciate that many or few criteria may be considered. In addition, other criteria can be used other than those described below. For example, linear regression, slope intercept, differentiation, weighted average, and other known mathematical models may be used in addition to or in lieu of the criteria listed below. Whether the number of criteria considered is few or many, all criteria will be used to reject unwanted noise, environmental influences, or motion in combination with the qualification of a pressure at which microcirculatory flow returns to the observation or measurement volume.

As a preliminary screening step, if motion artifact is severe enough to affect the rate of deflation, i.e. severe patient movement, the instrument will halt the test and inform the operator that the sensor/probe is unable to make accurate measurements.

Initially as a first criterion, $P_0$ must be within a valid range for the system to qualify an SPP value. If $P_0$ is not within a valid range, for example from approximately 1 mmHg to approximately 150 mmHg, the system will not indicate that a particular $P_0$ is an SPP value.

TABLE I

| PERFUSION MEASUREMENT | APPLIED CUFF PRESSURE <100 mm Hg | APPLIED CUFF PRESSURE > OR = 100 mm hg |
|---|---|---|
| <0.15% (Low) | 100% | 100% |
| 0.15 to 0.20% (Medium) | 50% | 50% |
| >0.20% (High) | 25% | 40% |

Another criterion is whether the perfusion increase is large enough relative to the measurement. If the perfusion increase is not large enough an SPP value will not be qualified. In interpreting "step size" (i.e. perfusion increase large enough from the prior measurement) the instrument uses a perfusion sensitive tolerance that progressively adjusts sensitivity thresholds as perfusion returns. This allows the system to qualify SPP values over a wide dynamic range while being less sensitive to motion transients. For example, if perfusion is very low then the instrument allows for the detection and rejection of motion artifact due to its perfusion sensitive tolerance. Referring to Table 1, preferred perfusion increases are noted. If the perfusion measurement is greater than 0.20% (i.e. high perfusion measurement) and the applied cuff pressure is less than 100 mmHg a perfusion increase of from 10% to 50% and preferably 25% relative to the prior measurement, is necessary. If the perfusion measurement is greater than 0.20% (i.e. high perfusion measurement) and the applied cuff pressure is greater than or equal to 100 mmHg a perfusion increase of from 20% to about 80%, and preferably 40%, relative to prior measurement is necessary. If the perfusion measurement is between 0.15 to 0.20% (i.e. medium perfusion measurement) and the applied cuff pressure is any valid pressure a perfusion increase of from 25% to 100%, and preferably 50%, relative to the prior perfusion measurement is necessary. If the perfusion measurement is less than 0.15% (i.e. low perfusion measurement) and the applied cuff pressure is any valid pressure a perfusion increase of from 50% to 200%, and preferably 100%, relative to the prior perfusion measurement is necessary.

Those skilled in the art will recognize that the foregoing criterion does not need to be limited to high, medium and low perfusion measurements or a few isolated points for applied cuff pressure, i.e. above and below 100 mmHg. These may be expressed as a continuous function of perfusion measurements or applied cuff pressure, or both.

Another criterion is whether the perfusion measurement under evaluation, i.e. $P_O$, is large enough, i.e. whether flow is above baseline. The perfusion should be preferably from between 0.05 to 0.2% and more preferably at least 0.10% at point $P_o$ or no skin perfusion pressure will be recorded.

Another criterion determines whether the "next steps," i.e. those following point $P_O$, are increasing or decreasing. Next steps must not be decreasing as this is not characteristic of a typical signature for returning microcirculatory flow to an observation volume with decreasing pressure. This fourth criterion focuses on the duration of increasing perfusion change. As microcirculation flow returns it produces a perfusion signal that increases and holds in a signature pattern. Motion artifact produces a perfusion signal that has more oscillatory content, thereby having greater tendencies to decrease.

TABLE 2

| Applied Cuff Pressure Range | Number of Following Steps |
|---|---|
| LOW | 1 |
| MEDIUM | 2 |
| HIGH | 3 |
| VERY HIGH | 5 |

When applied cuff pressure is low, i.e. preferably from about 0 to 20 mmHg and more preferably less than 15 mmHg, the number of next steps analyzed in determining whether next steps are increasing or decreasing is one. When the applied cuff pressure is in a medium range, for example from about 10 to 50 mmHg and more preferably from about 15 to about 20 mmHG, the number of next steps analyzed in determining whether next steps are increasing or decreasing is two. When applied cuff pressure is high, for example from about 40 to 120 mmHg and preferably greater than 50 mmHg but less than 100 mmHg, the number of next steps analyzed in determining whether next steps are increasing or decreasing is three. When pressure is very high, preferably from 80 to 150 mmHg, and most preferably greater than 100 mmHg, the number of next steps analyzed in determining whether next steps are increasing or decreasing is five. The higher the number of next steps being analyzed, i.e. N, the more confidence that the system has qualified an SPP value.

Another criterion for detecting and rejecting motion artifact is the profile of perfusion change. Microcirculation produces a perfusion signal that increases step-wise while motion produces a perfusion signal that has more oscillatory content. Changes that do not follow a perfusion return signature are ignored. Referring again to Table II, the perfusion change profile criterion for detecting and rejecting motion artifact is whether the specified number of steps following $P_1$ are at least at or above the perfusion value for $P_1$. These steps must not be decreasing. In other words, $P_2$ to $P_N$ must all be greater than $P_1$. This criterion is especially effective in rejecting motion, as those signals are not long-lived.

If all criteria are met the skin perfusion pressure system will qualify $P_0$ as the SPP value 38.

FIG. 5D depicts a model of what might be viewed if a patient has non-reactive hyperemia. In this case, the skin perfusion pressure system will recognize such a pattern as not characteristic of a normal perfusion measurement and no SPP value will be generated. In such cases, the perfusion data is reported and the physician is left to determine the SPP value for that test.

Sensor or Probe Placement Device

Conveniently, the surface perfusion pressure system in accordance with the present invention and as previously described may include a sensor or probe placement device for providing assurance of reproducible data included as a kit or provided separately.

Figure 6:
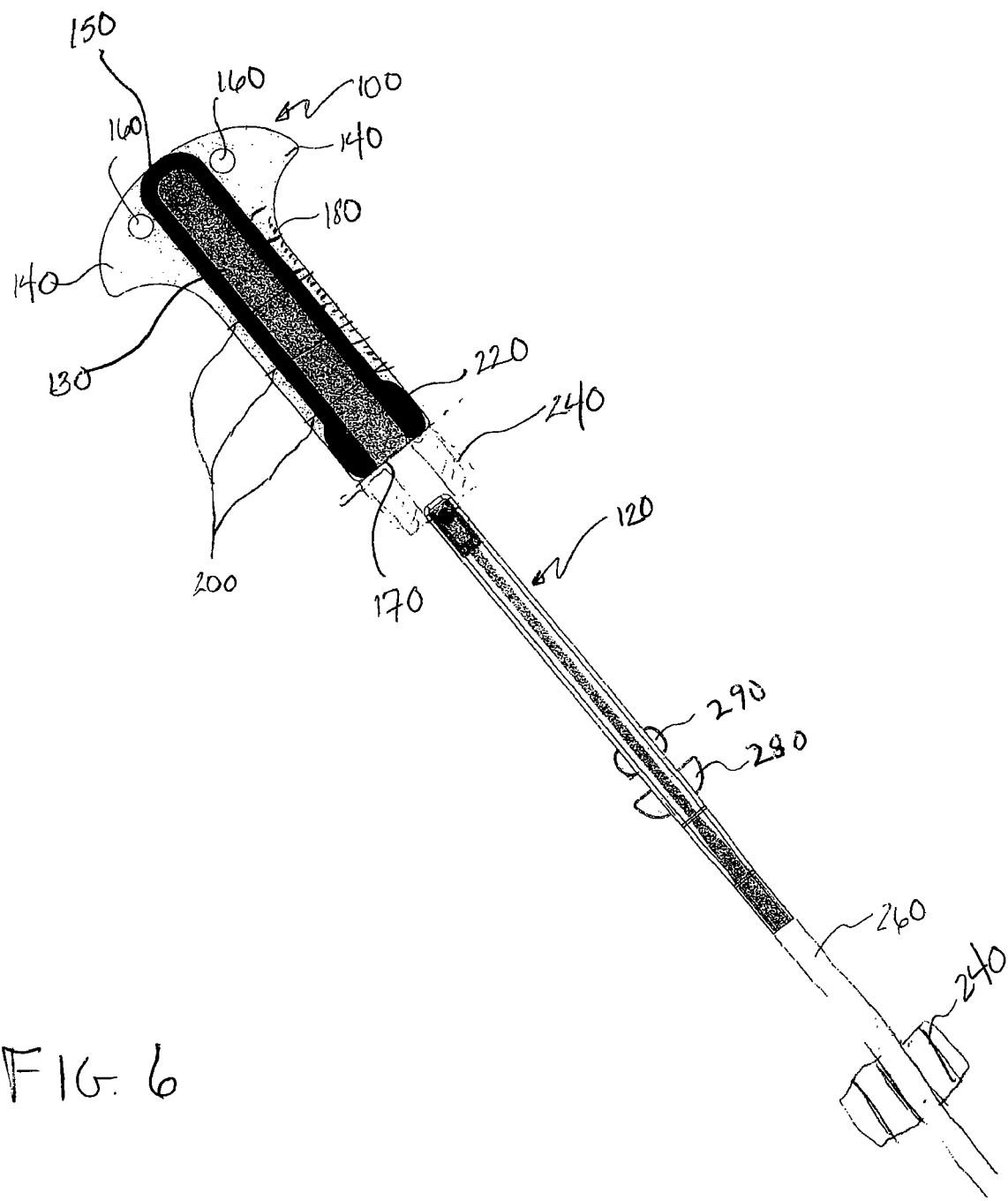
FIG. 6 is a top view of a sensor placement device in accordance with the present invention.

Referring to FIG. 6, there is depicted one embodiment of a sensor placement device 100 in accordance with the present invention. Sensor placement device 100 comprises a disposable sheath 130 sized to fit over an exemplary probe 120 used to measure microcirculatory blood flow. Those skilled in the art can appreciate that sensor placement device 100 can be used to cover and secure various shapes and sizes of probes, electrodes and other monitoring devices.

In a first embodiment of a sensor placement device 100 two opposing wings 140 located at a proximal end 150 are provided. Wings 140 can be wrapped around a patient's appendage in order to secure probe 120 thereon. Wings 140 can be variably sized to accommodate different sized appendages.

Sensor placement device 100 also includes two opposing position indicators 160 located at proximal end 150. Position indicators 160 are configured to allow health care providers to mark the placement of the sensor placement device 100. If additional measurements are required, the sensor placement device 100 and probe 120 can be positioned in the same location on the surface of the tissue thereby assuring reproducible data.

Sensor placement device 100 includes a measuring guide 180 positioned on at least one side of sheath 130. Measuring guide 180 is used to determine precise placement locations. Measuring guide 180 can be sized according to and used in combination with perforations 200. For example, units of measurement can be started at proximal end 150 with units of measurement increasing toward distal end 170. In this manner, measuring guide 180 is useful for measuring position locations even after perforated sections closer to distal end 170 are removed.

Distal end 170 of sheath 130 includes probe securing means receiving openings 220 positioned on opposing sides of sheath 130. Receiving openings 220 are sized and positioned to receive probe securing means 290. Receiving openings 220 are positioned such that the distal end of sheath 130 is perfectly aligned with sheath stops 280 on opposing sides of the cable end of probe 120. In this manner, sensor placement device 100 is firmly secured to probe 120. Receiving openings 220 depicted in FIGS. 6 and 7 are arcuate shaped. Those skilled in the art can appreciate that receiving openings can be sized or shaped to receive any size or shape of probe securing means 290.

In one embodiment, distal end 170 of sheath 130 is adjacent cable clamp 240. Cable clamp 240 is removable with an adhesive backing so that it can be separated from sensor placement device 100 and used to secure a cable 260 that extends between probe 120 and a monitoring system to a suitable surface.

The surface of sensor placement device 100 that contacts patient tissue may be treated with an adhesive coating. The adhesive coating may include any repositionable, pressure sensitive adhesive that does not interrupt physiological parameter monitoring. The adhesive coating is an inherently tacky, elastomeric, solvent-dispersible, solvent-insoluble pressure sensitive adhesive. In one embodiment, the adhesive coating is a monomer or polymer blend selected from the group consisting of alkyl acrylate, alkyl methacrylate ester, acrylic acid, methacrylic acid, itaconic acid, crotonic acid, maleic acid, fumaric acid, sulfoethyl methacrylate, and ionic monomers such as sodium methacryate, ammonium acrylate, sodium acrylate, trimethylamine p-vinyl benzimide, 4,4,9-trimethyl-4-azonia-7-oxo-8-oxa-dec-9-ene-1-sulphonate, N,N-dimethyl-N-(.beta.-methacryloxyethyloxy-ethyl) ammonium propionate betaine, trimethylamine methacrylimide, and 1,1-dimethyl-1-(2,3-dihydroxypropyl)amine methacrylimide. In another embodiment, the adhesive coating includes microspheres selected from the group consisting of acrylate, alkylacrylate and alkylacrylate ester monomers alone or in combination with vinyl monomers. The adhesive coating can be covered with a removable paper film used to maintain the tackiness of the adhesive coating during storage, transportation and other non-use situations.

The size and shape of the sensor placement device 100 can be varied. Logos or other art designs can be embossed on any part of the sensor placement device 100. The color of the sensor placement device 100 can also be a varied, including various patterns.

In use, because of their low cost, sensor placement devices 100 are dispensed in any convenient location such as operating rooms, intensive care units, clinic or hospital patient rooms, nursing areas, physician work stations and basically anywhere a probe 120 is used to monitor a physiological parameter. A healthcare professional may remove a sensor placement device 100 from a dispenser device, box or other storage container and inserts a probe 120 into distal end 170 of sheath 130. Openings 220 align with probe securing means 290. Sheath 130 fits over probe 120 with distal end 170 of sheath adjacent sheath stops 280 as depicted in FIG. 7. If sensor placement device 100 is too long for the measurement site, sections of sensor placement device 100 can be removed by tearing them off at desired perforations 200. After sensor placement device 100 is positioned over probe 120, the removable paper film (not shown), if applicable, can be removed and measuring guide 180 can be used to precisely position sensor placement device 100 on a desired part of a patient's tissue. Wings 140 can be wrapped around a patient's appendage such as a toe or foot to secure sensor placement device 100 thereon. Cable clamp 240 can be removed from distal end 170 of sheath 130 by tearing along perforations therebetween. Cable clamp 240 can then be used to secure cable 260 to a suitable support, such as a different part of patient's body, a hospital bed, etc.

Once positioned, cable clamp 240 can be detached and probe 120 can be removed from sensor placement device 100 without interrupting position of sensor placement device 100. A different probe 120 can then be inserted into sensor placement device 100, again without interrupting position of sensor placement device 100. In this manner, probes 120 can be changed without requiring new sensor placement devices 100 or repositioning sensor placement device 100. In the event that a new sensor placement device 100 is required, position indicators 160 can be marked such that a replacement sensor placement device 100 can be positioned in the same location as that of a previously placed sensor placement device 100. In this manner, interruptions to and errors in monitoring a physiological parameter can be minimized.

Once monitoring is complete, the healthcare professional removes sensor placement device 100 from the patient's tissue and simply disposes of it. In this manner, sensor placement device 100 prevents the transmission of infectious diseases while providing precise positioning, repositioning and securing of a probe to a patient's tissue.

Referring to FIG. 8, another embodiment of a sensor placement device 300 is shown. The sensor placement device 300 depicted in FIG. 8 can be used for measurements taken on larger extremities without the need for adhesives and is intended to remain on the patient at the measurement site until all measurements have been taken. Sensor placement device 300 may be constructed from a single sheet or multiple pieces. Sensor placement device 300 comprises an elastic wrap including a laminate of non-woven material and elastic fibers placed lengthwise to provide for elasticity. The fabric of sensor placement device 300 is a water-vapor permeable, non-woven polyester fabric containing longitudinal strands of polyester urethane, or elastane. The fabric is coated with a self-adherent substance that gives the bandage the ability to stick to itself but not to skin or clothing. The elastane strands impart a degree of elasticity to the bandage and the cohesive coating ensures that it does not become displaced once applied. The fabric is marketed under the trade name Coban™ and is available from 3M Company, St. Paul, Minn.

Sensor placement device 300 is depicted as being made from multiple pieces but those skilled the art will appreciate that a single sheet of appropriate size may be used. Clear plastic window 310 having first and second edges 312, 314 is placed over and secured to one side of sheet. Window 310 remains open at edges 312, 314 so that probe (not shown) can be easily inserted and removed. Those skilled in the art will appreciate that only one edge of window 310 needs to remain open to accomplish the purpose of sensor placement. If multiple pieces are used, window 310 is bonded at various sites 316 by heat or chemical sealing over the elastic wrap.

In operation the sensor placement device 300 is wrapped partially around a leg, for example, such that the window 310 is exposed. The probe (not shown) is positioned in window 310 and then the sensor placement device is wrapped further around the extremity over the probe and window securing the probe in place while measurements are taken.

Those skilled in the art will appreciate that the sensor placement device depicted in FIG. 6 can be positioned in window 310 to accomplish the measurement.

Although the description of the preferred embodiment has been presented, it is contemplated that various changes, including those mentioned above, could be made without deviating from the spirit of the present invention. It is therefore desired that the present embodiment be considered in all respects as illustrative, not restrictive, and that reference be made to the appended claims rather than to the foregoing description to indicate the scope of the invention.

What is claimed is:

1. An automated skin perfusion pressure measuring device comprising:
    an inflatable cuff;
    at least one blood flow sensor in communication with the cuff;
    at least one pressure sensor in communication with the cuff for reading pressure levels in the cuff;
    a pressure instrument in fluid communication with the cuff for inflation and deflation thereof, the pressure instrument comprising:
        a source of pressurized air;
        a conduit connected to the source of pressurized air and the cuff, thereby placing the source of pressurized air in fluid communication with the cuff;
        a microprocessor arranged to receive inputs from the first sensor and the second sensor, the microprocessor capable of controlling pressurized airflow to and from the cuff;
        a computer program executable by the microprocessor such that when executed, the computer program causes the microprocessor to:
            initiate an automatic inflation sequence resulting in a no flow condition;
            initiate an automatic deflation sequence;
            automatically qualify a perfusion measurement as an SPP value upon all conditions of a set of predetermined conditions being met during the deflation sequence.

2. The automated skin perfusion pressure measuring device of claim 1 wherein the at least one blood flow sensor is positioned underneath the cuff.

3. The automated skin perfusion pressure measuring device of claim 1 wherein the at least one blood flow sensor is positioned distal to the cuff.

4. The automated skin perfusion pressure measuring device of claim 1 wherein the at least one blood flow sensor is positioned inside a bladder within the cuff.

5. The automated skin perfusion pressure measuring device of claim 1 wherein the at least one blood flow sensor is selected from the group consisting of optical probe means, pulse oximeter means; optical plethemography means; motion detecting means; and laser Doppler means.

6. The automated skin perfusion pressure measuring device of claim 5 wherein the optical probe means comprises a laser transmitter fiber and a receiver photodiode.

7. The automated skin perfusion pressure measuring device of claim 5 wherein the optical probe means comprises a laser transmitter.

8. The automated skin perfusion pressure measuring device of claim 7 wherein the optical probe means further comprises a receiver photodiode.

9. The automated skin perfusion pressure measuring device of claim 5 wherein the optical probe means is connected to the pressure instrument via a fiber optic cable.

10. The automated skin perfusion pressure measuring device of claim 1 wherein one of said predetermined set of conditions comprise the perfusion measurement being from 1 mmHg to approximately 150 mmHg.

11. The automated skin perfusion pressure measuring device of claim 10 wherein if said perfusion measurement is less than 0.20% and said cuff pressure is less than 100 mmHg, then one of said predetermined set of conditions comprise a perfusion increase of from 10% to 50% from a previous perfusion measurement.

12. The automated skin perfusion pressure measuring device of claim 10 wherein if said perfusion measurement is greater than 0.02% and said cuff pressure is greater than or equal to 100 mmHg, then one of said predetermined set of conditions comprise a perfusion increase of from about 20% to about 80%.

13. The automated skin perfusion pressure measuring device of claim 10 wherein if said perfusion measurement is from 0.15% to about 0.20% and said cuff pressure is from 1 mmHg to about 150 mmHg, then one of said predetermined set of conditions comprise a perfusion increase of from about 25% to about 100%.

14. The automated skin perfusion pressure measuring device of claim 10 wherein if said perfusion measurement is less than 0.15% and said cuff pressure is from about 1 mmHg to about 150 mmHg, then one of said predetermined set of conditions comprise a perfusion increase of from about 50% to about 200%.

15. The automated skin perfusion pressure measuring device of claim 1 wherein one condition of the set of predetermined conditions comprises the perfusion measurement being from about 0.05% to about 0.2%.

16. The automated skin perfusion pressure measuring device of claim 1 wherein one of said predetermined set of conditions comprise whether steps following the perfusion measurement being tested for as an SPP value are decreasing.

17. The automated skin perfusion pressure measuring device of claim 16 wherein if the cuff pressure is less than 15 mmHg, the number of steps analyzed following the perfusion measurement being tested for as an SPP value is one.

18. The automated skin perfusion pressure measuring device of claim 16 wherein if the cuff pressure is in a range from 15 to less than 50 mmHg, the number of steps analyzed following the perfusion measurement being tested for as an SPP value is two.

19. The automated skin perfusion pressure measuring device of claim 16 wherein if the cuff pressure is in a range from 50 mmHg to less than 100 mmHg, the number of steps analyzed following the perfusion measurement being tested for as an SPP value is three.

20. The automated skin perfusion pressure measuring device of claim 16 wherein if the cuff pressure is greater than 100 mmHg, the number of steps analyzed following the perfusion measurement being tested for as an SPP value is five.

21. The automated skin perfusion pressure measuring device of claim 1 wherein one of said predetermined set of conditions comprise whether steps following the perfusion measurement being tested for as an SPP value are increasing.

22. The automated skin perfusion pressure measuring device of claim 21 wherein if the cuff pressure is less than 15 mmHg, the number of steps analyzed following the perfusion measurement being tested for as an SPP value is one.

23. The automated skin perfusion pressure measuring device of claim 21 wherein if the cuff pressure is in a range from 15 to less than 50 mmHg, the number of steps analyzed following the perfusion measurement being tested for as an SPP value is two.

24. The automated skin perfusion pressure measuring device of claim 21 wherein if the cuff pressure is in a range from 50 mmHg to less than 100 mmHg, the number of steps analyzed following the perfusion measurement being tested for as an SPP value is three.

25. The automated skin perfusion pressure measuring device of claim 21 wherein if the cuff pressure is greater than 100 mmHg, the number of steps analyzed following the perfusion measurement being tested for as an SPP value is five.

26. The automated skin perfusion pressure measuring device of claim 1 further comprising a display monitor operably connected to the pressure instrument and capable of displaying data.

27. The automated skin perfusion pressure measuring device of claim 26 wherein the display monitor is capable of displaying data pertaining to microcirculation within an observation volume of tissue.

28. The automated skin perfusion pressure measuring device of claim 26 wherein the display monitor is further capable of displaying data pertaining to cuff pressure.

29. The automated skin perfusion pressure measuring device of claim 28 wherein the display monitor is further capable of graphically displaying cuff pressure versus microcirculation within an observation volume of tissue.

30. The automated skin perfusion pressure measuring device of claim 1 wherein the cuff comprises a transparent window useable to observe the perfusion sensor.

31. The automated skin perfusion pressure measuring device of claim 1 further comprising a placement device for securing the at least one blood flow sensor in place during one or a plurality of measurements.

32. The placement device of claim 31 wherein the device is disposable.

33. The placement device of claim 31 further comprising a detachable sheath configured to secure said at least one blood flow sensor to a patient.

34. The placement device of claim 33 further comprising at least two wings positioned on opposing sides of a proximal end of said sheath; and receiving openings positioned on opposing side of a distal end of said sheath.

35. The sensor placement device of claim 34 wherein said wings include at least one position indicator therein.

36. The sensor placement device of claim 33 further comprising a measuring guide extending along at least one longitudinal side of said sheath.

37. The sensor placement device of claim 33 further comprising perforated sections, wherein a first perforated section is adjacent said distal end of said sheath, and further wherein a second perforated section is between said first perforated section and a third perforated section positioned nearer to said proximal end of said sheath.

38. The sensor placement device of claim 33 further comprising a cable clamp adjacent said distal end of said sheath and configured to be removed from said sensor placement device and positioned over a cable extending between said probe and a monitoring system.

39. The sensor placement device of claim 33 wherein said sheath includes an adhesive coating on a surface of sheath that is configured to secure said sensor placement device on a patient's tissue.

40. The blood flow measuring means placement device of claim 31 wherein said a placement device includes a self-adhesive fabric including a window thereon for inserting said blood flow measuring means.

41. A method of measuring skin perfusion pressure in a patient comprising:
providing an inflatable cuff in communication with at least one blood flow sensor;
initiating an automatic inflation sequence resulting in a no flow condition;
initiating an automatic deflation sequence; and
providing a microprocessor to automatically qualify a perfusion measurement as an SPP value upon all conditions of a predetermined set of conditions being met during the deflation sequence, wherein said predetermined set of conditions comprise (i) determining whether said perfusion measurement is within a range of from approximately 1 mmHg to approximately 150 mmHg; determining whether a perfusion increase from a prior measurement is greater than a predetermined minimum increase value; determining whether said perfusion measurement is from between 0.05% to 0.2%; and determining whether next steps following said perfusion measurement are not decreasing.

42. The method of claim 41 wherein initiating an automatic inflation sequence
comprises:
inflating the cuff to a first pressure;
verifying the blood flow sensor is detecting and measuring perfusion;
inflating the cuff to a second pressure;
verifying a no flow condition is achieved, otherwise:
increasing cuff pressure in predetermined increments until a no flow condition is achieved;
aborting the inflation sequence if the cuff pressure attains a predetermined maximum value before a no flow condition is achieved.

43. The method of claim 42 wherein inflating the cuff to a first pressure comprises inflating the cuff to 5 mmHg to 10 mmHg.

44. The method of claim 42 wherein inflating the cuff to a second pressure comprises inflating the cuff to approximately the patient's systolic pressure.

45. The method of claim 42 wherein increasing the cuff pressure in predetermined increments until a no flow condition is achieved comprises increasing the cuff pressure in predetermined increments of approximately 40 mmHg until a no flow condition is achieved.

46. The method of claim 41 wherein providing a microprocessor to automatically qualifying a perfusion measurement as an SPP value upon all conditions of a predetermined set of conditions being met during the deflation sequence further comprises identifying that the measured skin perfusion pressure is not the result of motion artifact.

47. The method of claim 41 wherein determining whether a perfusion increase from a prior measurement is greater than a predetermined minimum increase value comprises determining whether the perfusion increase is from 10% to 50% when the perfusion measurement is greater than 0.20% and the cuff pressure is less than 100 mmHg.

48. The method of claim 41 wherein determining whether a perfusion increase from a prior measurement is greater than a predetermined minimum increase value comprises determining whether the perfusion increase is from 20% to 80% when the perfusion measurement is greater than 0.20% and the cuff pressure is greater than or equal to 100 mmHg.

49. The method of claim 41 wherein determining whether a perfusion increase from a prior measurement is greater than a predetermined minimum increase value comprises determining whether the perfusion increase is from 25% to 100% when the perfusion measurement is from 0.15% to 0.20% and the cuff pressure is any valid cuff pressure.

50. The method of claim 41 wherein determining whether a perfusion increase from a prior measurement is greater than a predetermined minimum increase value comprises determining whether the perfusion increase is from 50% to 200% when the perfusion measurement is less than 0.15% and the cuff pressure is any valid cuff pressure.

51. The method of claim 41 wherein analyzing a number of subsequent perfusion measurements to determine whether the subsequent perfusion measurements are increasing or decreasing comprises analyzing one subsequent perfusion measurement if the cuff pressure is from 0 to 20 mmHg.

52. The method of claim 41 wherein analyzing a number of subsequent perfusion measurements to determine whether the subsequent perfusion measurements are increasing or decreasing comprises analyzing two subsequent perfusion measurements if the cuff pressure is from 10 to 50 mmHg.

53. The method of claim 41 wherein analyzing a number of subsequent perfusion measurements to determine whether the subsequent perfusion measurements are increasing or decreasing comprises analyzing three subsequent perfusion measurements if the cuff pressure is from 40 to 120 mmHg.

54. The method of claim 41 wherein analyzing a number of subsequent perfusion measurements to determine whether the subsequent perfusion measurements are increasing or decreasing comprises analyzing five subsequent perfusion measurements if the cuff pressure is from 80 mmHg to 150 mmHg.

55. The method of claim 41 wherein automatically qualifying a perfusion measurement as an SPP value upon all conditions of a predetermined set of conditions being met during the deflation sequence further comprises a condition selected from the group consisting of (i) when the cuff pressure is less than 15 mmHg and one subsequent perfusion measurement is increasing; (ii) when cuff pressure is from 15 to 20 mmHg and two subsequent perfusion measurements are increasing; (iii) when cuff pressure is from 50 to 100 mmHg and three subsequent perfusion measurements are increasing; (iv) when cuff pressure is 100 mmHg to 150 mmHg and five subsequent perfusion measurements are increasing.

56. A device for measuring skin perfusion pressure in a patient comprising:
    an inflatable cuff with perfusion sensing means for sensing perfusion in communication with said cuff;
    means for automatically inflating the cuff, according to an automatic inflation sequence, to a pressure resulting in a no flow condition;
    means for automatically deflating the cuff according to an automatic deflation sequence;
    means for continuously testing a series of perfusion measurements against a set of predetermined criteria to reject motion artifact and automatically qualify one of said perfusion measurements as an SPP value upon all conditions of the predetermined set of criteria being met.

57. The device of claim 56 wherein the automatic inflation sequence comprises: inflating the cuff to a first pressure;
    verifying the perfusion sensing means is detecting and measuring perfusion;
    inflating the cuff to a second pressure;
    verifying a no flow condition is achieved;
    increasing cuff pressure in predetermined increments until a no flow condition is achieved;
    aborting the inflation sequence if the cuff pressure attains a predetermined maximum value before a no flow condition is achieved.

58. The device of claim 56 wherein the automatic inflation sequence inflates the cuff to a first pressure of 5 mmHg to 10 mmHg.

59. The device of claim 56 wherein the automatic inflation sequence inflates the cuff to the patient's systolic pressure.

60. The device of claim 56 wherein the automatic inflation sequence increases the cuff pressure in predetermined increments of 40 mmHg until a no flow condition is achieved.

61. The device of claim 56 wherein the automatic deflation sequence comprises:
    (a) releasing pressure from the cuff at a desired controlled rate;
    (b) monitoring the deflation rate;
    (c) aborting the deflation sequence if the deflation rate is not substantially equal to the desired controlled rate;
    (d) analyzing whether a perfusion measurement qualifies as an SPP value using the testing means;
    (e) determining whether at least one automatic stop criterion has been met;
    (f) repeating steps (a)-(e) until at least one automatic stop criterion has been met;
    (g) reporting the SPP value from step (d) if any.

62. The device of claim 61 wherein the automatic deflation sequence further comprises:
    (a) after a predetermined number of repetitions of steps (a)-(e) in the absence of an acceptable SPP value, continuing to repeat steps (a)-(e) for a predetermined period of time;
    (b) displaying perfusion measurements on a display for physician interpretation.

63. The device of claim 61 wherein analyzing whether a perfusion measurement qualifies as an acceptable SPP value comprises identifying that the measured perfusion pressure is not the result of motion artifact.

64. The device of claim 61 wherein qualifying the SPP value comprises determining whether the perfusion measurement is within 1 mmHg to approximately 150 mmHg.

65. The device of claim 61 wherein analyzing whether a perfusion measurement qualifies an acceptable SPP value comprises determining whether a perfusion increase from a prior measurement is greater than a predetermined minimum increase value.

66. The device of claim 65 wherein determining whether a perfusion increase from a prior measurement is greater than a predetermined minimum increase value comprises determining whether at least one of the following criteria is met:
    a perfusion measurement greater than 0.20% when cuff pressure is less than 100 mmHg, and the perfusion increase is from 10% and 50%;
    a perfusion measurement greater than 0.20% when cuff pressure or greater than or equal to 100 mmHg, and the perfusion increase is from 20% and 80%;
    a perfusion measurement of from 0.15% to 0.20% when the cuff pressure is any valid cuff pressure, and the perfusion increase is from 25% to 100%;
    a perfusion measurement is less than 0.15%, when the cuff pressure is any valid cuff pressure, and the perfusion increase is from 50% to 200%.

67. The device of claim 65 wherein determining whether a perfusion increase from a prior measurement is greater than a predetermined minimum increase value comprises determining whether one of the following criteria is met:
    a perfusion measurement greater than 0.20% with a cuff pressure less than 100 mmHg, and the perfusion increase is 25%;
    a perfusion measurement greater than 0.20% with a cuff pressure greater than or equal to 100 mmHg, and the perfusion increase is 40%;
    a perfusion measurement equal to from 0.15% to 0.20% with any valid cuff pressure, and the perfusion increase is 50%;

a perfusion measurement less than 0.15% with any valid cuff pressure, and the perfusion increase is 100%.

68. The device of claim 61 wherein analyzing whether a perfusion measurement qualifies as an acceptable SPP value comprises determining whether the perfusion measurement is from 0.05% to 0.2%.

69. The device of claim 61 wherein analyzing whether a perfusion measurement qualifies an acceptable SPP value comprises:
   comparing the perfusion measurement to subsequent perfusion measurements to determine whether the subsequent perfusion measurements are increasing or decreasing;
   qualifying the perfusion measurement as an SPP value if all conditions of the predetermined set of criteria are met, wherein one of the criteria met is selected from the group consisting of (i) a cuff pressure of from 0 to 20 mmHg and one subsequent perfusion measurement is increasing; (ii) a cuff pressure of from 10 to 50 mmHg and two subsequent perfusion measurements are increasing; (iii) a cuff pressure of from 40 to 120 mmHg and three subsequent perfusion measurements are increasing; (iv) a cuff pressure greater than 80 mmHg and five subsequent perfusion measurements are increasing.

70. The device of claim 69 wherein qualifying the perfusion measurement as an SPP value comprises qualifying the perfusion measurement as an SPP value if all conditions of the predetermined set of criteria are met, wherein one of the criteria met is selected from the group consisting of (i) a cuff pressure less than 15 mmHg and one subsequent perfusion measurement is increasing; (ii) a cuff pressure from 15 to 20 mmHg and two subsequent perfusion measurements are increasing; (iii) a cuff pressure of from 50 to 100 mmHg and three subsequent perfusion measurements are increasing; (iv) a cuff pressure of from 100 mmHg to 150 mmHg and five subsequent perfusion measurements are increasing.

71. The device of claim 61 wherein analyzing whether a perfusion measurement qualifies as an SPP value comprises:
   defining a perfusion change profile;
   determining whether the perfusion measurement is one of a sequence of perfusion measurements that fits the perfusion change profile.

72. The device of claim 71 wherein defining a perfusion change profile comprises defining a profile in which a measured perfusion measurement meets the criteria selected from the group consisting of (i) when cuff pressure is from 0 to 20 mmHg, a next subsequent perfusion measurement is not decreasing; (ii) when cuff pressure is from 10 to 50 mmHg, two immediately subsequent perfusion measurements are not decreasing; (iii) when cuff pressure is from 40 to 120 mmHg, three immediately subsequent perfusion measurements are not decreasing; (iv) when cuff pressure is greater than 80 mmHg, five immediately subsequent perfusion measurements are not decreasing.

73. The device of claim 72 wherein defining a perfusion change profile comprises defining a profile in which a measured perfusion measurement meets the criteria selected from the group consisting of (i) when cuff pressure is less than 15 mmHg, a next subsequent perfusion measurement is not decreasing; (ii) when cuff pressure is from 15 to 20 mmHg, two immediately subsequent perfusion measurements are not decreasing; (iii) when cuff pressure is from 50 to 100 mmHg, three immediately subsequent perfusion measurements are not decreasing; (iv) when cuff pressure is from 100 mmHg to 150 mmHg, five immediately subsequent perfusion measurements are not decreasing.

* * * * *